United States Patent [19]

Glattstein et al.

[11] Patent Number: 4,812,413

[45] Date of Patent: Mar. 14, 1989

[54] REAGENT, PROCESS AND KIT FOR DRUG DETECTION

[75] Inventors: Baruch Glattstein; Abraham Aserin, both of Jerusalem, Israel

[73] Assignee: Erez Forensic Technology, Ltd., Israel

[21] Appl. No.: 26,614

[22] Filed: Mar. 17, 1987

[51] Int. Cl.⁴ .................. G01N 33/00; G01N 21/78
[52] U.S. Cl. .......................... 436/92; 422/61; 436/901; 436/903
[58] Field of Search .............. 422/61; 436/92, 96, 436/111, 112, 127–129, 901, 903

[56] References Cited

U.S. PATENT DOCUMENTS

| | | | |
|---|---|---|---|
| 3,415,717 | 12/1968 | Avakian | 436/903 |
| 3,585,004 | 6/1971 | Mast | 436/903 |
| 3,880,896 | 4/1975 | Phillips et al. | 260/397.3 |
| 3,915,639 | 10/1975 | Friedenberg | 436/901 |
| 3,955,926 | 5/1976 | Fischer | 436/92 |
| 4,051,186 | 9/1977 | Kaplan | 564/340 |
| 4,104,027 | 8/1978 | Carroll | 436/92 |
| 4,110,078 | 8/1978 | Zelonis | 436/92 |
| 4,152,307 | 5/1979 | Shibahara et al. | 524/376 |
| 4,339,276 | 7/1982 | Yokoyama et al. | 428/485 |

FOREIGN PATENT DOCUMENTS

| | | | |
|---|---|---|---|
| 0132313 | 1/1985 | European Pat. Off. | 436/901 |
| 1426177 | 2/1976 | United Kingdom | 436/92 |

OTHER PUBLICATIONS

G. Norwitz and P. N. Kelsher, "Amer. Chem. Soc.", vol. 53, pp. 1238–1240, 1961.

Primary Examiner—Barry S. Richman
Assistant Examiner—Timothy M. McMahon

[57] ABSTRACT

The invention provides an aerosol spray reagent for the presumptive identification of cocaine, cocaine salts and phencyclidene comprising cobalt thiocyanate, a polyol, an aliphatic solvent, a nonionic emulsifier and a silicon antifoam agent, as well as providing a multi-reagent test kit for the presumptive identification of cocaine, cocaine salts and phencyclidene comprising a first aerosol spray reagent as defined and a second reagent which produces a color reaction in the presence of trace amounts of a diazotisable amine.

15 Claims, No Drawings

REAGENT, PROCESS AND KIT FOR DRUG DETECTION

FIELD OF THE INVENTION

The present invention relates to a process and test kit for the presumptive identification of cocaine and phencyclidine.

BACKGROUND OF THE INVENTION

As will be realized, on numerous occasions a police officer has to determine whether or not a suspected material contains a prohibited drug and thus quickly establish probable cause.

Often, the laboratory is closed, or many miles away, and he has no way of making this determination. A test kit can help an officer detect the presence of such drugs of abuse.

The quickest test known for drug identification is a color test in which the response of the drugs to a specific reagent makes it possible to assign the drug to one or more classes.

In order to obtain sufficient evidence to detain a suspected drug peddler or drug user, chemical spot test kits have been commercially developed and are used by many law enforcement agencies for the identification of narcotics and drugs of abuse.

Most of the commercial test kits for the presumptive identification of cocaine are based on contacting cocaine and its salts with cobalt thiocyanate solutions which results in the formation of a relatively water insoluble turquoise complex.

The relative simplicity of the cobalt thiocyanate test made its use feasible outside the laboratory and created a demand for a variation with increased specificity.

The standard Scott Test (L. J. Scott, Specific Field Test for Cocaine, Microgram, VI, 179(1973), is based on the use of cobalt thiocycanate as incorporated in a commercial test kit which contains the chemicals required to perform the test in a prefilled, hermetically sealed glass ampules.

There are three glass ampules:
(1) Cobalt thiocyanate reagent in a 1:1 water glycerine solution;
(2) Concentrated hydrochloric acid; and
(3) chloroform The glass ampules are placed into a pouch. The pouch is folded at the top, and a clip is placed over the fold which seals the package.

The following is the recommended test procedure when using this kit:
(1) Remove the plastic clip from the test pack and open the pouch.
(2) Place the suspect cocaine into the pouch, tap or jar the test package, making sure most of this falls to the bottom of the pack.
(3) Refold the pouch at the original fold point and replace the clip securely, sealing the package.
(4) The cobalt thiocyanate ampule should then be broken, releasing the reagent to mix with the suspect material. This can be accomplished by squeezing the center with the thumb and forefinger. When breaking the ampule, the fingers are pushing against smooth glass walls. If the ampule is squeezed at the extreme top or bottom, it could conceivably break through the plastic pouch. Therefore apply even pressure at the center of the ampule. No attempt should be made to crush the small glass particles after the ampule is broken.
(5) With the suspect material in the test package and the reagent released, gently shake or agitate.
(6) If turquoise blue precipitate is formed the second and the third ampules should be broken.
(7) Before discarding the test pack, remove clip and add one measure of acid neutralizer.
(8) Reseal test packs with clips and discard in a tamper-free disposal unit.

This method has several disadvantages:
(1) Complicated procedure;
(2) It uses corrosive concentrated hydrochloric acid; and
(3) Trace amount of cocaine cannot be detected.

Despite this known disadvantage, in the last ten years no one has proposed or commercialized an improved test kit which would ameliorate these problems.

THE INVENTION

Bearing the above in mind there is now provided an aerosol spray reagent for the presumptive identification of cocaine, cocaine salts and phencyclidene comprising cobalt thiocyanate, a polyol, an aliphatic solvent, a non-ionic emulsifier and a silicon antifoam agent.

While the above reagent is primarily a test for cocaine and its salts, phencyclidine, more commonly known as "angel dust", is also a major drug of abuse, the identification of which is also grounds for detaining a suspected drug peddler or drug user, and said drug also gives a positive test with the reagent of the present invention.

The reagent of the present invention has many advantages over other reagents presently in use including the following:
(1) It is economical in that only about 0.2 ml is enough for one test.
(2) It is simple to operate.
(3) Because the solution is not poisonous it can be used for testing large suspected areas. (This advantage cannot be accomplished by ampules).
(4) Trace amounts can readily be detected and distinct turquoise colored spots appear on the surface of the suspect surface even with a short gentle spraying of a quick light coat of reagent.

In hindsight the combination of a Scott reagent, with an aerosol may appear simple however it is to be noted that despite the wide felt need no one suggested this solution for the last ten years. Furthermore the incorporation of a Scott Reagent in an aerosol was not accomplished by simple combination. As is known Butane and Freon 12 are the common propellents used in prepackaged aerosols spray.

If one were to attempt to put these propellents and the Scott reagent together two disadvantages would prevent it from functioning at all:
(1) The propellents are immiscible with the solution and thus two phases are formed.
(2) The solution is relased from the spray as foam that makes the test impossible.

Thus only after experimentation and incorporation of both an emulsifier which rendered the solution homogeneous and an antifoam agent was a usable aerosol reagent achieved.

The known cobalt thiocyanate reagent test for cocaine is based on the fact that cocaine is very soluble in water. By adding a polyhydroxy compound to an aqueous reagent, the solubility of other drugs is reduced to zero, thus preventing a false positive reaction with drugs such as heroin, methadone, quinine, etc., however, cocaine is still soluble in such a mixture to give a good response.

It is noted that increasing the concentration of the polyhydroxy compound reduces the false positive responses, but complicates the procedure by using a viscous solution that reacts slowly and with which trace amounts cannot be detected.

It has, however, now also been discovered that by using an aliphatic solvent, preferably a halogenated alkane such as Freon 12, Freon 113 or dichloromethane and a non-ionic emulsifier, the viscosity of a reagent containing cobalt thiocyanate and a polyhydroxy compound is dramatically reduced without reducing sensitivity.

Thus, the present invention provides an improved cobalt thiocyanate reagent which is fast reacting, highly sensitive to even trace amounts of drug and which does not give false positive results.

In said reagent said solvent is preferably a halogenated alkane selected from Freon 12, Freon 113 and dichloromethane and said polyol is preferably selected from glycerol, propylene glycol, sorbitol: sorbitan mono-oleate (Span 80) and said emulsifier can be sorbitan trioleate (Span 85); and emulsifier is preferably Emcol 14 manufactured by Witco N.Y. or Mirj which is a polyethyleneglycol monooleate manufactured by ICI-Atlas, Great Britain.

A preferred reagent according to the present invention comprises about 1 to 3% cobalt thiocyanate, 20 to 50% water, 20 to 60% of a polyol, 20 to 50% of a halogenated alkane solvent, 0.5 to 1.5% of a non-ionic emulsifier and 0.1 to 2% of a silicon antifoam agent.

In another aspect of the present invention there is provided a multireagent test kit and a process for the presumptive identification of cocaine, cocaine salts and phencyclidene based thereon.

The Scott test used today by the Customs service is based on using test tubes in three stages:

A. Using cobalt thiocyanate reagent in a 1:1 water:-gylcerine solution that forms the characteristic blue precipitate with cocaine. In this stage, there are still four drugs that will react with the same color reaction as cocaine:
(1) Phencyclidine (PCP);
(2) Dibucaine;
(3) Butacaine;
(4) Methapyrilene.

The following two stages exclude these four drugs.

B. Addition of concentrated hydrochloric acid to form a clear pink solution.

C. Addition of chloroform which turns blue as the complexed cocaine is partitioned into the organic phase.

This complicated three step test does not take into account the fact that both dibucaine and methapyrilene are so rare that the chances that a suspected sample will in fact be one of these compounds is so negligible as to approach zero.

Thus, of the above five mentioned drugs, only butacaine is both commonly available and not a drug of abuse and a test which would eliminate butacaine would allow for presumptive identification of cocaine or phencyclidine with cobalt thicocyanate.

With the above in mind, in accordance with the present invention, there is now provided a process for the presumptive identification of cocaine, cocaine salts and phencyclidene, comprising applying an aerosol spray cobalt thiocyanate reagent as hereinbefore defined to a first sample of a suspected drug and applying to a second sample of the drug a second agent which produces a color reaction in the presence of trace amounts of a diazotisable amine.

The invention also provides a multi-reagent test kit for the presumptive identification of cocaine, cocaine salts and phencyclidene comprising a first aerosol spray reagent as hereinbefore defined and a second reagent which produces a color reaction in the presence of trace amounts of a diazotisable amine.

In its preferred embodiments, said second reagent comprises a nitrite salt, a compound which couples with diazonium salts and an acid.

Both said first reagent and said second reagent (without the nitrite component thereof) are preferably separately packaged in aerosol containers and dispensers in combination with a propellant selected from compressed air, fluoro-hydrocarbon, a chloro-fluoro-hydrocarbon, $CO_2$ gas, nitrous oxide or $N_2$ gas although simple pump (without propellant) dispensers can also be used.

With regard to the second reagent of the multireagent kit of the present invention said reagent gives a characteristic color reaction in the presence of trace amounts of butacaine as well as with other local anaesthetics that have diazotisable amino groups and which may react with the first reagent.

In said second reagent, said nitrite salt is preferably selected from potassium nitrite and sodium nitrite, and said coupling agent is preferably selected from N-(1-naphthyl)-ethylenediamine, α-naphthylamine, N-alkyl-α-naphthyl amine and chloride salts thereof.

Suitable acids for the reagent according to the invention are solid organic acids, for example citric acid, oxalic acids and aqueous acids, for example, phosphoric acid and hydrochloric acid.

For said second reagent there is preferably used potassium nitrite, N-(1-naphthyl)-ethylene diamine dihydrochloride and 1% phosphoric acid.

In an especially preferred embodiment of the present invention, the nitrite salt of said second reagent is incorporated in a sheet of absorbent substrate such as Benchkote® manufactured by Whatman of England.

A sample to be tested is placed on said sheet and sprayed with the first reagent. If upon spraying a characteristic turquoise blue color is formed, then a few drops of the remaining components of the second reagent are also sprayed on said sample on said treated sheet.

If a red to red-violet color appears, this is characteristic of Butacaine, but if the color does not appear, the probability is that the sample is cocaine, a cocaine salt or phencyclidene.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example embodiments of the present invention only and are presented in the cause of providing what is believed to be the most useful and readily understood description of formulation procedures as well as of the principles and conceptual aspects of the invention. Unless otherwise stated, the standard accepted convention is utilized in the appended examples and claims that—when solids and/or liquids are mixed in a composition—percentage is by weight; when liquids are mentioned in ratios, the ratios are by volume; and the designation of a solid in a liquid is percentage weight by volume.

Preferred components for a first reagent to be dispensed from an aerosol spray are described in examples 1–5 hereinafter while example 6–8 relate to components of the second reagent and example 9 describes use thereof.

EXAMPLE 1

A prepackaged aerosol spray of the first reagent is prepared containing 60% (W/W) of 1% (W/V) cobalt thiocyanate in glycerine:water (2:1) (V/V); 38% (W/W) Freon 12; 1% (W/W) silicone antifoam (Fluka); and 1% (W/W) Emcol-14® emulsifier.

EXAMPLE 2

A prepackaged aerosol spray of the first reagent is prepared containing 60% of 2% cobalt thiocyanate in glycerine:water (1:1), 38% Freon 12, 1% silicone antifoam (Fluka) and 1% Emcol-14® emulsifier.

EXAMPLE 3

A prepackaged aerosol spray of the first reagent is prepared containing 50% of 1% cobalt thiocyanate in propyleneglycol:water (1:1), 48% Freon 113, 1% Silicon Antifoam (Mayer U.S.A.) and 1% Mirj® (ICI-Atlas Great Britain).

EXAMPLE 4

A solution of first reagent to be administered by dropper is prepared containing 60% of 1% cobalt thiocyanate in glycerine:water (1:1), 39% dichloromethane and 1% Mirj® (ICI-Atlas Great Britain).

EXAMPLE 5

A solution of first reagent to be administered by dropper is prepared containing 60% of 1% cobalt thiocyanate in glycerine:water (6:4), 39% $CHCl_3$ and 1% Emcol®-14 emulsifier.

EXAMPLE 6

A second reagent of the present invention is prepared in the following manner:

Filter paper (Benchkote, Whatman) is impregnated with a solution which contains 1% $KNO_2$ in 100 ml distilled water.

A prepackaged aerosol spray is prepared comprising 1% N-1-(naphthyl)ethylenediaminedihydrochloride in aqueous 1% phosphoric acid —59%, Freon 12—40% and Emcol 14-1%.

EXAMPLE 7

A second reagent of the present invention is prepared in the following manner:

Filter paper (Benchkote, Whatman) is impregnated with a solution which contains 1% $KNO_2$ in 100 ml distilled water.

A prepackaged aerosol spray is prepared comprising 1% α-naphthylamine and 1% hydrochloric acid.

EXAMPLE 8

A second reagent of the present invention is prepared in the following manner:

Filter paper (Benchkote, Whatman) is impregnated with a solution which contains 1% $KNO_2$ in 100 ml distilled water.

A prepackaged aerosol spray is prepared comprising 1% N-methyl-α-naphthylamine and 1% citric acid.

EXAMPLE 9

A suspect substance is placed on a paper impregnated with potassium nitrite and a few drops of the first reagent (Cobalt-thiocynate) solution of example 5 are added which stain the paper with a turquoise color. The spray of example 6 was then applied. When a red to red violet appears the suspect substance is butacaine or some other drug that reacts with the first reagent and has a diazotisable amine group. Cocaine and PCP will not react with the second reagent and thus if the turquoise color remains the sample is presumed to be cocaine, a salt of cocaine of PCP.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. An aerosol spray reagent for the presumptive identification of a prohibited drug such as cocaine, cocaine salts and phencyclidene which comprises cobalt thiocyanate, a polyol in which said drugs are selectively soluble, a halogenated alkane propellant, a non-ionic emulsifier different from said polyol and a silicon anti-foam agent.

2. A reagent according to claim 1 wherein said is a halogenated alkane aerosal propellent selected from is the group consisting of Freon 12, Freon 113 and dichloromethane.

3. A reagent according to claim 1 wherein said polyol is selected from the group consisting of gylcerol, propyleneglycol, and sorbitol.

4. The reagent according to claim 1 wherein said emulsifier is selected from the group consisting of sorbitan mono-oleate sorbitan trioleate and polyethyleneglycol monooleate.

5. The reagent according to claim 1 comprising about 1 to 3 wt. % of cobalt thiocyanate, 20 to 50 wt. % of water, 20 to 60 wt. % of said polyol, 20 to 50 wt. % of said halogenated alkane aerosol propellant, 0.5 to 1.5 wt. % of said non-ionic emulsifier, and 0.1 to 2 wt. % of said silicon antifoam agent.

6. A mult-reagent test kit for the presumptive identification of cocaine, cocaine salts and phencyclidene comprising a first aerosol spray reagent according to claim 1 contained in a first containing means and a second reagent which produces a color reaction in the presence of trace amounts of a diazotisable amine contained in a second containing means.

7. A multi-reagent test kit for the presumptive identification of cocaine, cocaine salts and phencyclidene according to claim 6 wherein said second reagent comprises a nitrite salt, a diotizable coupling agent and an acid.

8. The multi-reagent test kit according to claim 7 wherein said nitrite salt is selected from the group consisting of potassium nitrite and sodium nitrite.

9. The multi-reagent test kit according to claim 7 wherein said coupling agent is selected from the group consisting of N-(1-naphthyl)-ethylenediamine, α-naphthylamine, N-alkyl-α-naphthylamine and the chloride salts thereof.

10. The multi-reagent test kit according to claim 7 wherein said acid is selected from the group consisting of citric acid, oxalic acid, phosphoric acid, and hydrochloric acid.

11. The multi-reagent test kit according to claim 7 wherein said nitrite salt is provided in dry form impregnated in a sheet of absorbent substrate, said sheet defining said second containing means and said acid is contained in a third containing means.

12. The multi-reagent test kit according to claim 7 wherein said second reagent comprises potassium nitrite, N-(1-naphthyl)-ethylenediamine dihydrochloride and 1% phosphoric acid.

13. A multi-reagent kit according to claim 7 wherein said second reagent comprises N-(1-naphthyl)-ethylene diamine dihydrochloride and 1% phosphoric acid and said second containing means comprising aerosol spraying means such that said second reagent can be provided in an aerosol spray.

14. A process for the presumptive identification of cocaine, cocaine salts and phenylcyclidene, comprising the steps of spraying an aerosol spray reagent comprising cobalt thiocyanate, a polyol, an aliphatic aerosol propellant, a non-ionic emulsifier different from said polyol and a silicon antifoam agent, to a first sample of a suspected drug and then contacting therewith a second reagent which produces a color reaction in the presence of a diazotisable amine.

15. The process according to claim 14 wherein said second reagent is applied to a second sample of said drug.

* * * * *